(12) United States Patent
Wang

(10) Patent No.: US 7,087,030 B2
(45) Date of Patent: Aug. 8, 2006

(54) AMBULATORY HIP FIXATION-TRACTION SPLINT SET

(76) Inventor: Ming-Hua Wang, Room 601, No.21, Dong Bao Road, Hangzhou, Zhejiang, PRC (CN) 310016

( * ) Notice: Subject to any disclaimer, the term of this patent is extended or adjusted under 35 U.S.C. 154(b) by 527 days.

(21) Appl. No.: 10/359,670

(22) Filed: Feb. 7, 2003

(65) Prior Publication Data

US 2004/0054309 A1    Mar. 18, 2004

Related U.S. Application Data

(60) Provisional application No. 60/410,126, filed on Sep. 13, 2002.

(51) Int. Cl.
*A61F 5/00* (2006.01)
(52) U.S. Cl. .............................. 602/5; 602/19; 602/23; 128/845
(58) Field of Classification Search ................ 128/845; 602/10, 12, 19, 32, 5; 135/68–74
See application file for complete search history.

(56) References Cited

U.S. PATENT DOCUMENTS

| | | | | |
|---|---|---|---|---|
| 3,272,210 A * | 9/1966 | Boruvka | .................. | 135/69 |
| 4,254,948 A * | 3/1981 | Jacobs | .................. | 482/68 |
| 6,003,532 A * | 12/1999 | Pi | .................. | 135/67 |
| 6,286,529 B1 * | 9/2001 | Olivera | .................. | 135/82 |

* cited by examiner

*Primary Examiner*—Michael A. Brown
(74) *Attorney, Agent, or Firm*—Raymond Y. Chan; David and Raymond Patent Group

(57) ABSTRACT

An ambulatory hip fixation-traction splint set includes a supporting frame having an upper end arranged for positioning below an armpit of a treated patient and a lower end extending to position below a hip portion of the treated patient, and a side splint assembly including a flexible guiding frame having first and second end portions mounted to the supporting frame wherein the guiding frame has a curved guiding surface adapted for fixing on a side body of the treated patient to retain the side body thereof at a fixation position. Therefore, the ambulatory hip fixation-traction splint set not only keeps the fracture area of the patient in fixation position but also assists the patient to have a suitable movement so as to enhance the recovery of the fracture area.

8 Claims, 5 Drawing Sheets

AMBULATORY HIP FIXATION-TRACTION SPLINT SET

CROSS REFERENCE OF RELATED APPLICATION

This is a regular application of a provisional application, application No. 60/410,126, filed on Sep. 13, 2002.

BACKGROUND OF THE PRESENT INVENTION

1. Field of Invention

The present invention relates to a splint, and more particularly to an ambulatory hip fixation-traction splint set which is capable of applying to an patient with hip fracture, hip disease or other disorders to not only keep the injury area of the patient in fixation position but also assist the patient to have a suitable movement so as to enhance the recovery of the injury area.

2. Description of Related Arts

According to the National Institute of Arthritis and Musculoskeletal and Skin Diseases (NIAMS), Osteoporosis is one of the major health risks for tens of millions of Americans. Every year osteoporosis is responsible for more than 1.5 million fractures, which include 300,000 hip fractures, approximately 700,000 vertebral fractures, 250,000 wrist fractures, and more than 300,000 other fractures. Patients with osteoporosis may have fractures induced from normal movement action, such as lifting, bending, or accidental falling. Therefore, there is a strong demand for treatment methods for osteoporosis. And in fact, together with those having bones fractures or the like by accident, there is a great number of patients suffering from bones diseases, bone fractures or related problems such as broken bones, bones fractures or other disorders.

Immobilization is one of the most popular and efficient treatment methods for bones diseases or support system related problems, such as bone fractures, broken legs, and hip diseases or other disorders. Orthoses, such as braces, splints or casts, are widely developed and used for external fixation. Existing methods of immobilization by orthoses as external fixation for areas such as neck, elbow, wrist, knee, or ankle are proved to be very effective and efficient. Yet there is still no effective or efficient immobilization method for hip area or its vicinities.

Among existing methods of immobilization by external fixation for hip or thigh diseases, casts or splints for fixing and guiding the fracture or broken parts in position are commonly used. However, either a spica cast or a traditional splint is not an ideal method for immobilization, especially for the old with hip fracture or hip disease. These two common methods, a spica cast or a traditional splint, pose high risk of complications or side effects, such as pressure sores or pneumonia. In case if too much space is left for allowing movement, these two methods are inadequate for fixation and immobilization.

In order to provide chances of exercises for patients, traditional traction can be achieved for the reduction and fixation of unstable fracture. Unfortunately, traditional traction including both skeletal traction and skin traction must be applied on a lying surface such as a bed and balanced by cords with pulleys and weights. Therefore, patients with hip fractures or bone diseases must be laid on a bed if traditional traction is applied for assisting movement. However, since patients with hip fractures or bone diseases usually require a long period of time for recovery, and traditional traction cannot assist patients to have movement out of the bed, patients will ultimately required to lie on the bed for a long period of time. If suitable movement or exercise cannot be accompanied as a recovery treatment, many problems such as pressure sores, pneumonia, or even deterioration of healthy organs of the patient may probably appear and hence adversely affect the health of the patient.

Suitable traction or guidance should be provided at the same time for facilitate movement as appropriate movement or exercise is effective, useful or required for recovery. Currently, many methods or equipment are developed for aiding movement or exercise by traction, yet these methods are either ineffective for traction or impose great inconvenience to the patient. The patient always needs to seek for guidance and support in movement and relies heavily on third party, or the patient is required to lie on a bed all the time.

Accordingly, a walking stick is widely used in different situations for providing support to the old, to hikers, to the weak, or to those with broken or fracture bones such as broken ankles, broken fibula, broken shinbone, broken kneecap (patella) or broken thigh bone (femur). When the walking stick is used for providing support to a patient or for orthopedic purposes, it is particularly important that the walking stick is capable of providing a rigid, yet protective and flexible support according to the body movement so as to prevent the collapse of the walking stick and worsen a broken or weakened part of the patient. The walking stick is highly effective for patients having bone problems such as broken ankles, fibula, shinbone, kneecap or thigh bone. However, in the case of hip fractures or hip diseases, a walking stick is far from adequate for assisting movement or traction.

For example, if a patient having a hip fracture uses the walking stick for standing or even walking, he will probably fall down and worsen his situation. Hip fracture will lead to chain collapses of support system right from the hip, even though his legs have no problems. If he tries to stand or walk with a stick, great pressure will be applied on his hip, especially when there is a weaken part, i.e., the fracture part. This kind of pressure will be concentrated on his hip and will cause displacement or distortion of his hip, spreading of the fracture area, or even breakage the fracture area. Therefore, existing walking stick is not suitable for assisting movement by traction. The support of a walking stick is not concrete and adequate. If the pressure, which is originally concentrated on the hip, can be spread to and shared by other parts of the body, the possibility of standing or even walking will be high increased.

There are also different methods for aiding movement for the injured person. For example, a hanging weight support associated with a pulley and a cord, and a bed comprising a rear part which may be uplifted are used together, so that the patient may use his own body weight in aiding movement by traction, such as lifting his lower body or stretching himself, or supporting and moving himself for gaining a certain degree of exercise or moving ability. However, the injured person is still required to lie on his own bed.

There are many disadvantages in lying on a bed. Recovery of our skeleton or support system usually takes time, and it may take several weeks, months or even years. If a patient is required to lie on a bed for a long time, his respiratory system, blood circulation system, digestive system or other healthy parts of support system will be adversely affected or deteriorated due to lack of movement or exercise. In the worst case, certain diseases or symptoms such as inflammation, swollen blood vessels, or even serious complications such as pneumonia may be induced. These diseases are particularly harmful and disastrous to the old and/or the weak patient.

Furthermore, recovery always relies heavily on the emotional stability and status, of the patient. If movement ability of the patient is limited or prohibited, serious emotional instability may be caused. When the patient feels that he needs to depend on others or he could not take care himself, he may be upset and unhappy. And this kind of emotional instability will be unavoidably happened from time to time when the movement ability of the injured is lost or limited. Therefore, any equipment which can aid in movement or allowing the patient to have certain degree of movement will greatly promote the recovery of the injured person.

Therefore, there is a need to have a kind of splint having a guidance and support for aiding movement, and that the splint is capable of providing a rigid, yet protective and flexible support according to the movement of the injured person so as to prevent any possible pressure or force applied on the injured.

SUMMARY OF THE PRESENT INVENTION

A main object of the present invention is to provide an ambulatory hip fixation-traction splint set which is capable of applying to an patient with hip fracture, hip disease or other disorders to not only keep the fracture area of the patient in fixation position but also assist the patient to have a suitable movement so as to enhance the recovery of the fracture area.

Another object of the present invention is to provide an ambulatory hip fixation-traction splint set, wherein a curvature of a guiding surface of a side splint assembly can be selectively adjusted to fittedly fix to the patient so as to retain the fracture area of the patient in position.

Another object of the present invention is to provide an ambulatory hip fixation-traction splint set which comprises a supporting frame adapted for distributing a weight of the patient while the fracture area of the patient is retained in the fixation position, so that the patient is allowed to have the suitable movement without pressuring on the fracture area thereof.

Another object of the present invention is to provide an ambulatory hip fixation-traction splint set, wherein the guiding frame is capable of providing a retraction force against the weight of the patient so as to minimize the weight of the patient pressured on the fraction area thereof and enhance the mobility of the patient.

Another object of the present invention is to provide an ambulatory hip fixation-traction splint set, wherein a footstep is adjustably mounted on the supporting frame for supporting the patient's leg, so as to further minimize the weight of the patient pressured on the fraction area thereof through the patient, especially during walking.

Another object of the present invention is to provide an ambulatory hip fixation-traction splint set which comprises a front splint assembly adapted for fixing on a front side of the patient to limit the forward bending movement of the body of the patient so as to further retain the fracture area of the patient in the fixation position during movement.

Another object of the present invention is to provide an ambulatory hip fixation-traction splint set, wherein no expensive or complicated structure is required to employ in the present invention in order to achieve the above mentioned objects. Therefore, the present invention successfully provides an economic and efficient solution for not only providing a substantial support to retain the fracture area of the patient in the fixation position but also allowing the patient to have a suitable movement or exercise to be accompanied as a recovery treatment.

Accordingly, in order to accomplish the above objects, the present invention provides an ambulatory hip fixation-traction splint set, comprising:

a supporting frame having an upper end arranged for positioning below an armpit of a treated patient and a lower end extending to position below a hip portion of the treated patient; and a side splint assembly, comprising:

a flexible guiding frame having first and second end portions mounted to the supporting frame wherein the guiding frame has a curved guiding surface adapted for fixing on a side body of the treated patient to retain the side body thereof at a fixation position; and a curvature adjusting device provided on the supporting frame to adjustably retain a distance between the first and second end portions of the guiding frame so as to selectively adjust a curvature of the guiding surface with respect to the supporting frame for fitting on the side body of the treated patient.

These and other objectives, features, and advantages of the present invention will become apparent from the following detailed description, the accompanying drawings, and the appended claims.

DETAILED DESCRIPTION OF THE PREFERRED EMBODIMENT

Figure 1:
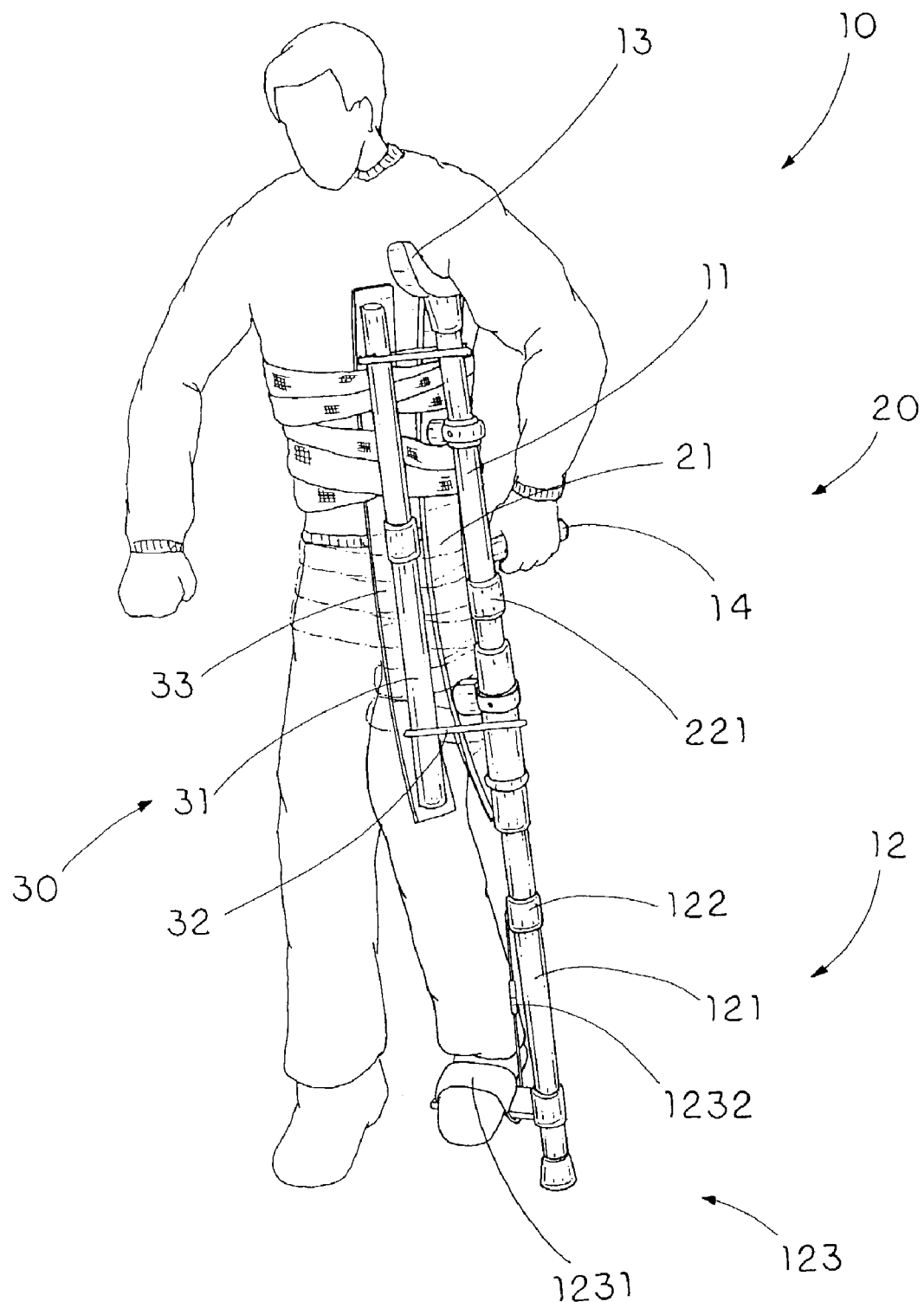
FIG. 1 is a perspective view of an ambulatory hip fixation-traction splint set according to a preferred embodiment of the present invention.
Figure 2:
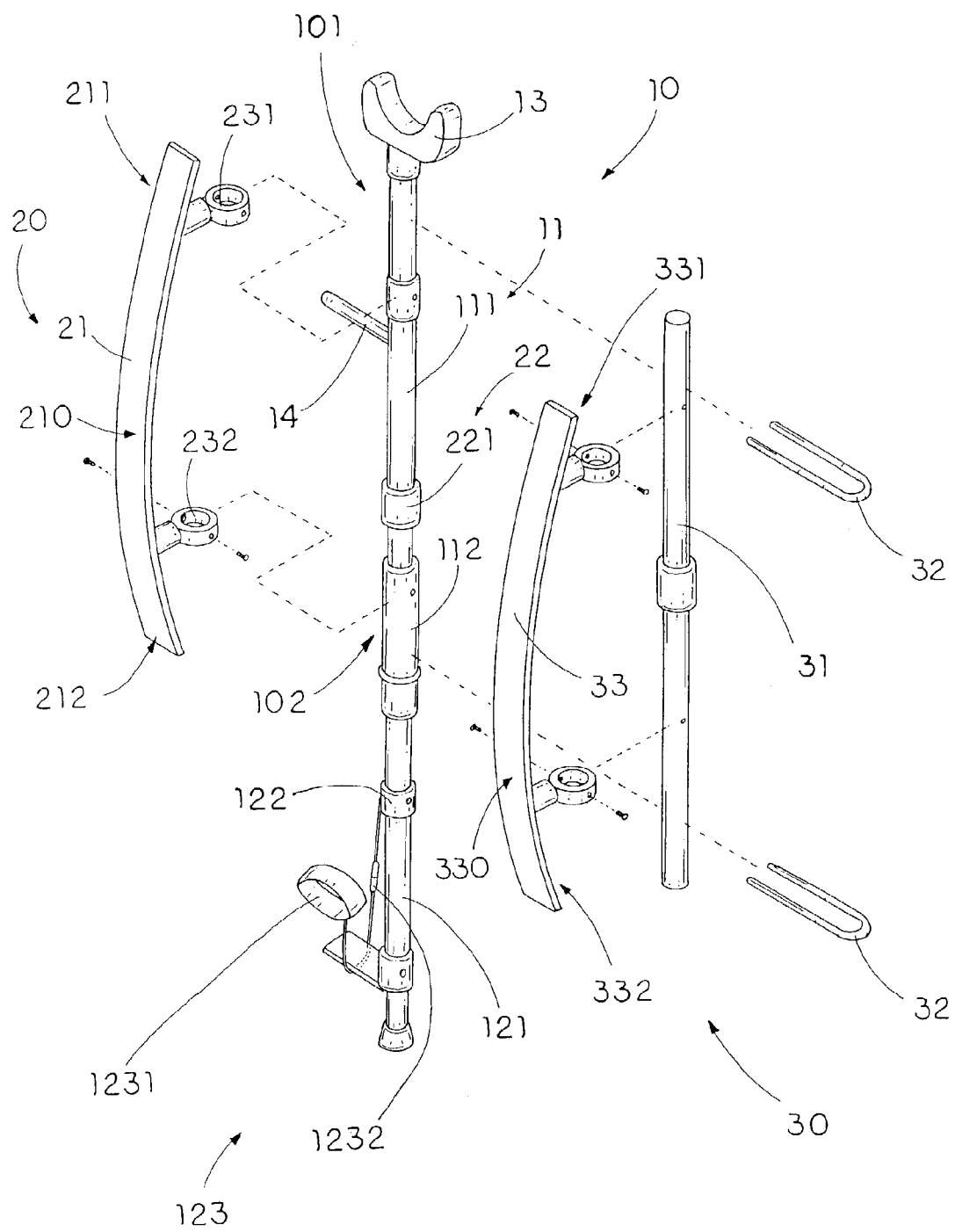
FIG. 2 is an exploded perspective view of the ambulatory hip fixation-traction splint set according to the above preferred embodiment of the present invention.
Figure 3:
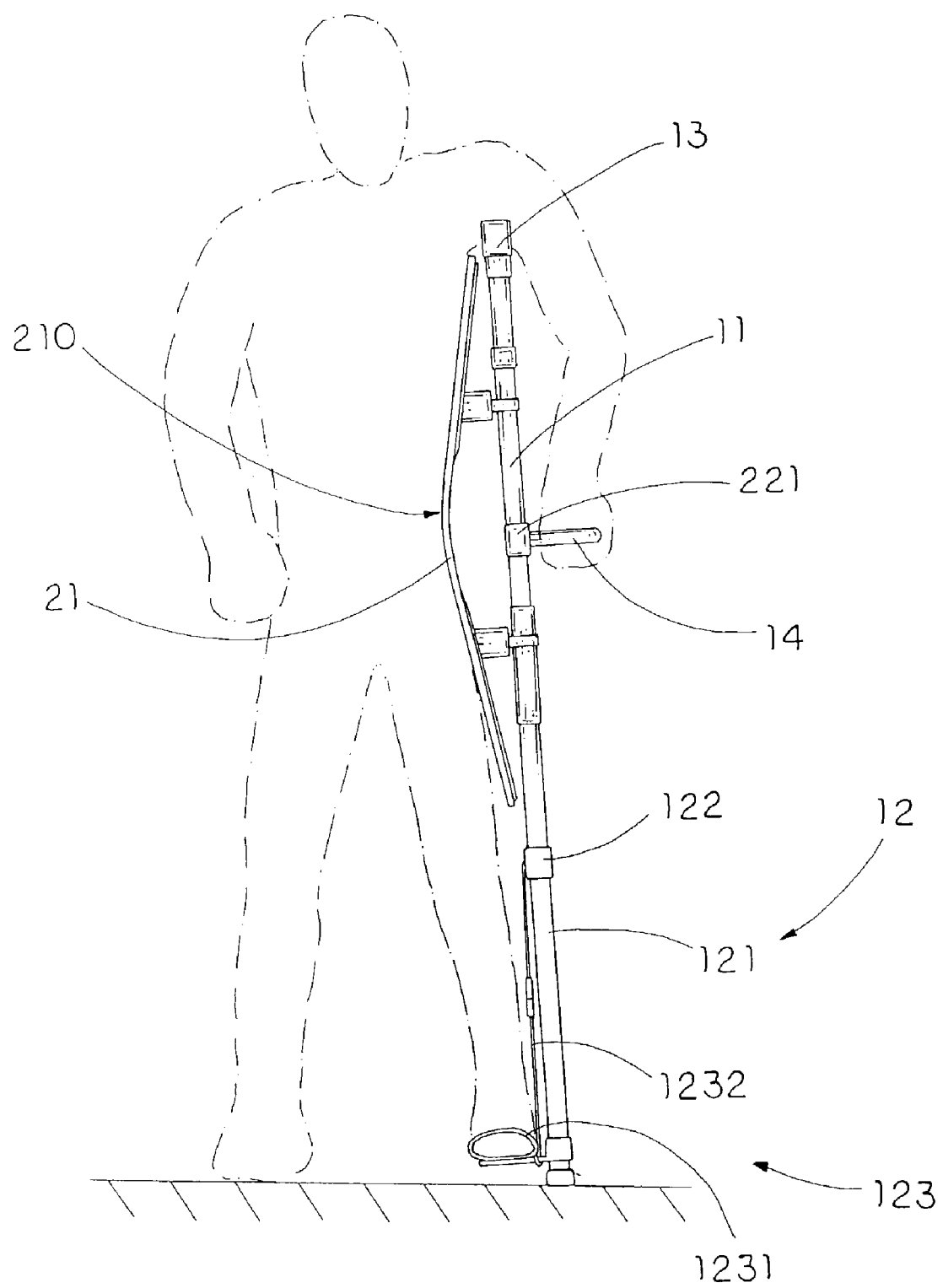
FIG. 3 is a front view of the ambulatory hip fixation-traction splint set without front supporting splint according to the above preferred embodiment of the present invention.

Referring to FIGS. 1 through 3 of the drawings, an ambulatory hip fixation-traction splint set according to a preferred embodiment of the present invention is illustrated, wherein the ambulatory hip fixation-traction splint set is capable of retaining a treated patient having a fraction area at the side body thereof, such as rib fraction, waist fraction, or hip fraction, at a fixation position.

The ambulatory hip fixation-traction splint set comprises a supporting frame 10 having an upper end 101 arranged for positioning below an armpit of the treated patient and a lower end 102 extending to position below a hip portion of the treated patient.

The ambulatory hip fixation-traction splint set further comprises a side splint assembly 20 comprising a flexible guiding frame 21 having first and second end portions 211, 212 mounted to the supporting frame 10 wherein the guiding frame 21 has a curved guiding surface 210 adapted for fixing on the side body of the treated patient to retain the side body thereof at a fixation position, and a curvature adjusting device 22 provided on the supporting frame 10 to adjustably retain a distance between the first and second end portions 211, 212 of the guiding frame 21 so as to selectively adjust a curvature of the guiding surface 210 with respect to the supporting frame 10 for fitting on the side body of the treated patient.

According to the preferred embodiment, the supporting frame 10 comprises an elongated body supporting member 11 having a length adapted for fittedly extending from the armpit of the treated patient to a hip portion thereof to rigidly support an upper body of the patient. The body supporting member 11 is preferably made of rigid but light weight material such as metal in such a manner that when the treated patient incorporates with the ambulatory hip fixation-traction splint of the present invention, the body supporting member 11 of the supporting frame 10 functions as a body support to prevent any unwanted body movement, especially upper body and hip movements, of the treated patient.

The first end portion 211 of the guiding frame 21 is securely affixed to the body supporting member 11 below the upper end 101 thereof via a first frame joint 231 and the second end portion 212 of the guiding frame 21 is securely affixed to the body supporting member 11 above the lower end 102 thereof via a second frame joint 232 wherein the guiding surface 210 is provided between the first and second end portions 211, 212 of the guiding frame 21 and facing towards the side body of the treated patient. It is worth to mention that due to the flexibility of the guiding frame 21, the guiding frame 21 is capable of providing a retraction force on the guiding surface 210 against the side body of the treated patient so as to enhance the flexible body support of the present invention.

Figure 4:
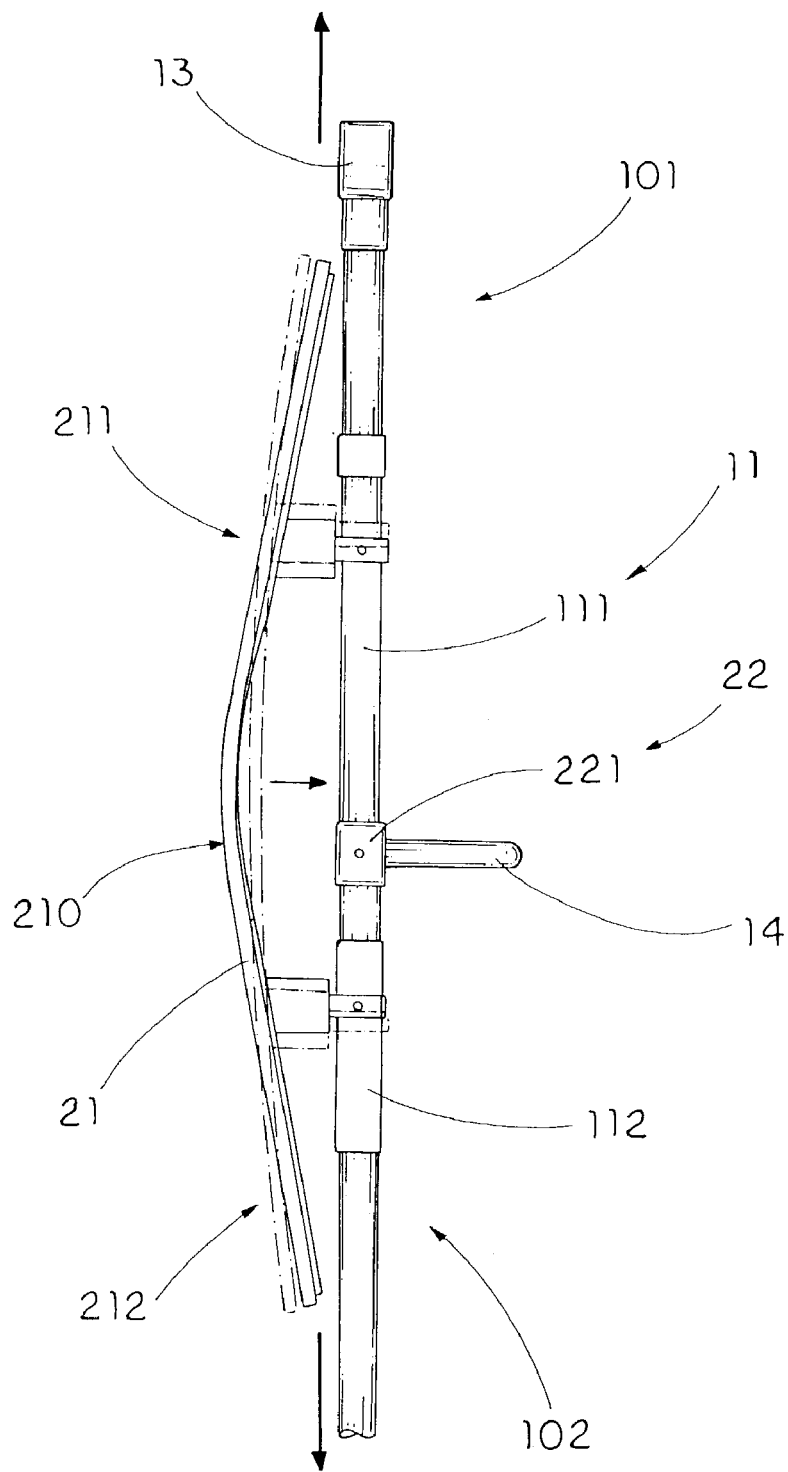
FIG. 4 is a side view of a curvature adjusting means of the ambulatory hip fixation-traction splint set according to the above preferred embodiment of the present invention.

As shown in FIG. 4, the body supporting member 11 comprises an upper tubular body 111 and a lower tubular body 112 slidably and coaxially mounted to the upper tubular body 111 in such a manner that when the upper tubular body 111 is slid away from the lower tubular body 112, the distance between the upper and lower ends 101, 102 of the body supporting member 11 is substantially increased, and when the upper tubular body 111 is slid towards to the lower tubular body 112, the distance between the upper and lower ends 101, 102 of the body supporting member 11 is substantially decreased. In other words, the length of the body supporting member 11 can be selectively adjusted to fit the body size of the treated patient.

The curvature adjusting device 22 comprises a frame locker 221 mounted on the body supporting member 11 to lock up the upper tubular body 111 with the lower tubular body 112 so as to securely retain the distance between the upper and lower ends 101, 102 of the body supporting member 11. Since the first and second end portions 211, 212 of the guiding frame 21 are securely affixed to the body supporting member 11 at two end portions thereof, the guiding frame 21 is bent more outwardly with respect to the body supporting member 11 while reducing the distance between the first and second end portions 211, 212 of the guiding frame 21 so as to increase the curvature of the guiding surface 210. Likewise, while increasing the distance between the first and second end portions 211, 212 of the guiding frame 21, the guiding frame 21 is bent less outwardly with respect to the body supporting member 11 so as to reduce the curvature of the guiding surface 210, as shown in FIG. 4.

Therefore, the frame locker 221 is capable of locking the upper tubular body 111 with the lower tubular body 112 to lock up the distance between the upper and lower ends 101, 102 of the body supporting member 11 so as to securely retain the curvature of the guiding surface 210. In other words, the curvature of the guiding surface 210 can be selectively adjusted by the position of the frame locker 221 along the body supporting member 11 for fitting the curvature of the side body of the treated patient.

Accordingly, the curvature of the guiding surface 210 of the guiding frame 21 is pre-adjusted to fit the side body of the treated patient. Therefore, the curvature of the treated patient should be pre-measured before placing the guiding frame 21 thereon. Also, the curvature of the guiding surface 210 of the guiding frame 21 should be locked to prevent the distortion of the guiding frame 21 after being used so as to affect the fixation treatment of the present invention.

Figure 5:
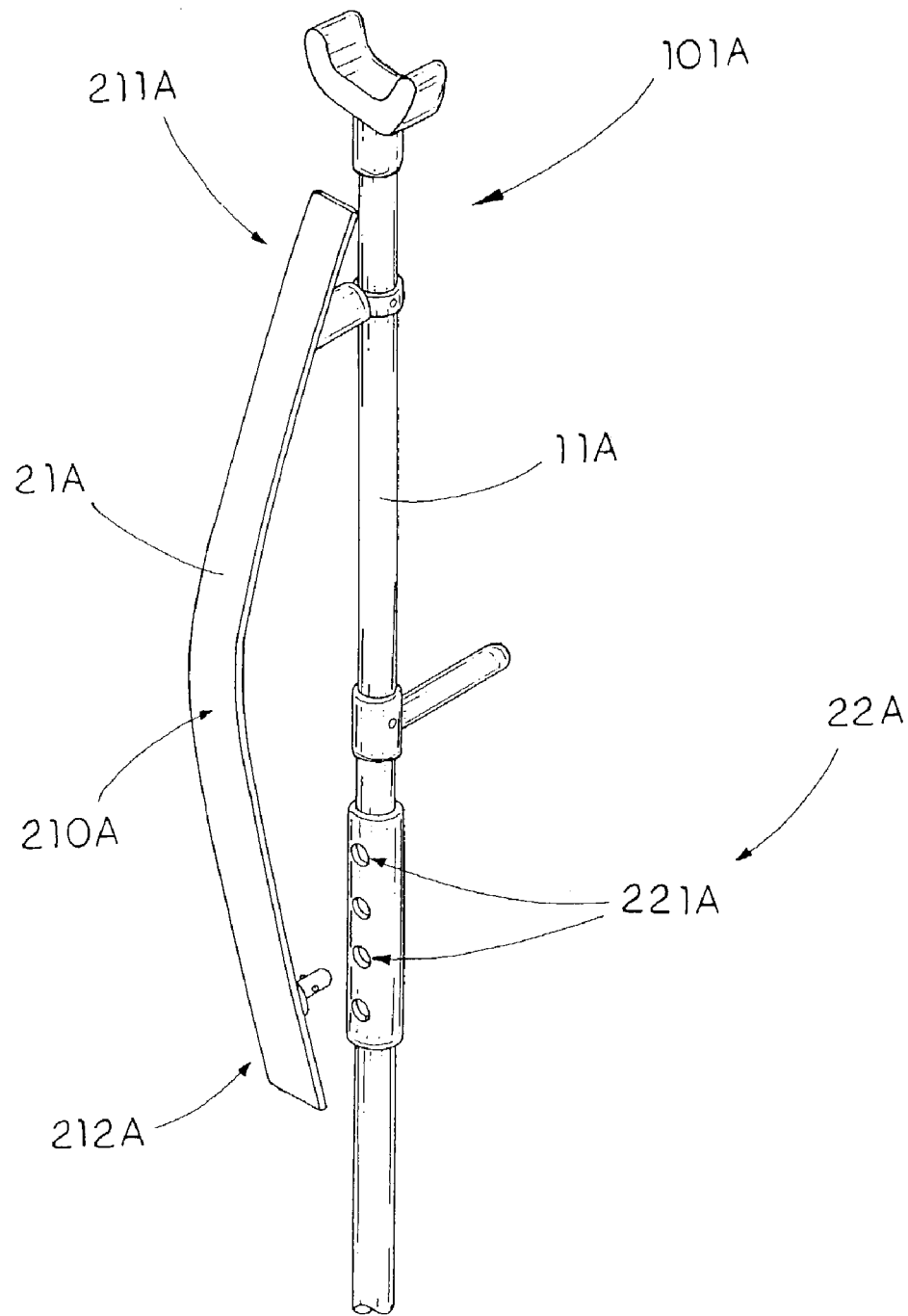
FIG. 5 illustrates an alternative mode of the curvature adjusting means of the ambulatory hip fixation-traction splint set according to the above preferred embodiment of the present invention.

FIG. 5 illustrates an alternative mode of the curvature adjusting device 22A which contains a plurality of engaging slots 221A spacedly provided on the body supporting member 11A wherein the first end portion 211A of the guiding frame 21A is securely affixed to the body supporting member 11A below the upper end 101A thereof and the second end portion 212A of the guiding frame 21A is selectively engaged with one of the engaging slots 221A so as to adjust the distance between the first and second end portions 211A, 212A of the guiding frame 21A and the curvature of the guiding surface 210A thereof.

In order to fix the guiding surface 210 on the side body of the treated patient, a bandage may be used to wrap around the upper body of the treated patient with the body supporting member 11, so that side body of the treated patient is substantially supported by the guiding frame 21 at the fixation position to prevent any unwanted movement of the upper body of the treated patient.

The supporting frame 10 further comprises a ground supporting member 12 comprising a ground stand 121 slidably and downwardly extended from the body supporting member 11 as a walking stick for distributing a weight of the treated patient to the ground, and a locking member 122 provided at the body supporting member 11 to lock up the body supporting member 11 with the ground supporting member 12 so as to selectively adjust a supportive portion of the ground stand 121 with respect to a height of the treated patient. In other words, the ground stand 121 is capable of adjustably extending from the body supporting member 11 to lengthen the supportive portion of the ground stand 121 for a taller treated patient and to shorten the supportive portion of the ground stand 121 for a shorter treated patient.

In addition, the supporting frame 10 further comprises an armpit resting support 13 mounted at the upper end 101 of the body supporting frame 11 for supporting the armpit of the treated patient so as to enhance the weight, especially the upper body, of the patient distributing to the ground through the ground stand 121. Moreover, a handgrip 14 is transversely extended from the body supporting frame 11 at a predetermined position for the treated patient so that the treated patient is able to hold the handgrip 14 to stabilize the body weight during movement.

The ground supporting member 12 further comprises a hip-stress releasing unit 123 which comprises a footstep retainer 1231 transversely extended from the ground stand 121 and means 1232 for applying a pulling force on the footstep retainer 1321 towards a ground end of the ground stand 121.

Accordingly, the pulling means 1232 comprises a pulley system comprising an elongated element extended from the ground stand 121 to the footstep retainer 1231 through a pulley in such a manner that by selectively adjusting a length of the elongated element, the footstep retainer 1231 is slidably moved towards the ground end of the ground stand 121. In other words, when the treated patient is supported by the ground stand 121 while the foot of the treated patient is retained at the footstep retainer 1231, the pulling means 1232 substantially applies a pulling force to slightly pull the foot of the treated patient downwardly with respect to the hip portion thereof, so as to minimize the stress around the hip portion of the treated patient. Therefore, the hip-stress releasing unit 123 is capable of providing a cushion effect and absorbing a reaction force at the hip portion of the treated patient, so as to reduce the pressure against on the fraction area of the treated patient.

It is worth to mention that when the treated patient has a waist or hip fraction, the treated patient is unable to walk since the leg of the treated patient is not strong enough to support the weight thereof while highly increasing the pressure on the fraction area through the leg. Therefore, the leg of the treated patient is capable of being supported by the footstep retainer 1231 to minimize the stress on the fraction area through the leg during movement. It is worth to mention that a distance between the armpit resting support 13 and the ground end of the ground stand 121 should be adjusted as a distance between the armpit of the treated patient with respect to the ground in order to optimize the body weight support of the present invention.

As shown in FIG. 2, the ambulatory hip fixation-traction splint set further comprises a front splint assembly 30 comprising a side supporting member 31, a side extension frame 32 transversely extended from the body supporting member 11 to securely connect to the side supporting member 31, and a flexible front guiding frame 33 having first and second end portions 331, 332 spacedly mounted to the side supporting member 31 and a curved front guiding surface 330 adapted for fixing on a front body of the treated patient to retain the front body thereof at a fixation position, as shown in FIG. 1. In other words, the side body and the front side body of the patient are substantially supported by the guiding frame 21 and the front guiding frame 33 respectively to prevent any unwanted movement of the treated patient, as shown in FIG. 1.

Accordingly, the dimension of the front splint assembly 30 is pre-measured for the user according to the size of the user's body such that the angle between the front guiding frame 33 and the guiding frame 21 is pre-adjusted by the position of the side supporting member 31 through the side extension frame 32. Therefore, the broken or fracture part of the patient must be immobilized in a predetermined position so as to eliminate the risk of bone displacement or even distortion.

Accordingly, the front guiding frame 33 is constructed as the guiding frame 21 that is capable of adjusting a curvature of the front guiding surface 331 for fittedly fixing on the front body of the treated patient, i.e. the side portion of the chest of the treated patient. Moreover, the front guiding frame 33 is capable of being rotated with respect to the body supporting member 11 through the side supporting member 32 to adjust the position of the front guiding surface 330 facing towards the front body of the treated patient.

For example, the treated patient has a tendency to lean his or her upper body forward wherein the forward leaning movement of the treated patient may hurt the fraction area thereof. Therefore, when the front body of the treated patient is supported by the front splint assembly 30, the upper body of the treated patient is retained in a fixation position so as to prevent any pressure applying on the fraction area of the treated patient.

One skilled in the art will understand that the preferred embodiment and its alternative of the present invention as shown in the drawings and described above is exemplary only and not intended to be limited.

It will thus be seen that the objects of the present invention have been fully and effectively accomplished. It embodiments have been shown and described for the purposes of illustrating the functional and structural principles of the present invention and is subjected to change without departure from such principles, such as the curvature adjusting device or the shape of the body supporting member. Therefore, this invention includes all modifications encompassed within the spirit and scope of the following claims.

What is claimed is:

1. An ambulatory hip fixation-traction splint set, comprising:
    a supporting frame comprising a body supporting member having an upper end arranged for positioning below an armpit of a treated patient and a lower end extending to position below a hip portion of said treated patient; and
    a side splint assembly, which comprises:
    a flexible guiding frame having first and second end portions mounted to said upper and lower ends of said body supporting member respectively wherein said guiding frame has a curved guiding surface adapted for fixing on a side body of said treated patient to retain said side body thereof at a fixation position and for providing a retraction force against said side body of said treated patient; and
    a curvature adjusting device provided on said supporting frame to adjustably retain a distance between said first and second end portions of said guiding frame so as to selectively adjust a curvature of said guiding surface with respect to said supporting frame for fitting on said side body of said treated patient, wherein said curvature adjusting device contains a plurality of engaging slots spacedly provided on said body supporting member, wherein said first end portion of said guiding frame is securely affixed to said body supporting member and said second end portion of said guiding frame is selectively engaged with one of said engaging slots so as to adjust said distance between said first and second end portions of said guiding frame and said curvature of said guiding surface thereof.

2. An ambulatory hip fixation-traction splint set, comprising:
    a supporting frame comprising a body supporting member having an upper end arranged for positioning below an armpit of a treated patient and a lower end extending to position below a hip portion of said treated patient wherein said supporting frame further comprises a ground supporting member comprising a ground stand downwardly extended from said body supporting member for distributing a weight of said treated patient through said ground stand, wherein said ground supporting member further comprises a hip-stress releasing unit which comprises a footstep retainer transversely extended from said ground stand and means for applying a pulling force on said footstep retainer towards a ground end of said ground stand; and
    a side splint assembly comprising a flexible guiding frame having first and second end portions mounted to said upper and lower ends of said body supporting member respectively wherein said guiding frame has a curved guiding surface adapted for fixing on a side body of said treated patient to retain said side body thereof at a fixation position and for providing a retraction force against said side body of said treated patient.

3. An ambulatory hip fixation-traction splint set, comprising:
a supporting frame comprising a body supporting member having an upper end arranged for positioning below an armpit of a treated patient and a lower end extending to position below a hip portion of said treated patient, wherein said supporting frame further comprises a ground supporting member comprising a ground stand downwardly extended from said body supporting member for distributing a weight of said treated patient through said ground stand, wherein said ground stand is slidably extended from said body supporting member, wherein said supporting frame further comprises a locking member provided at said body supporting member to lock up said body supporting member with said ground stand so as to selectively adjust a supportive portion of said ground stand from said body supporting member with respect to a height of said treated patient, wherein said ground supporting member further comprises a hip-stress releasing unit which comprises a footstep retainer transversely extended from said ground stand and means for applying a pulling force on said footstep retainer towards a ground end of said ground stand; and
a side splint assembly, which comprises:
a flexible guiding frame having first and second end portions mounted to said upper and lower ends of said body supporting member respectively wherein said guiding frame has a curved guiding surface adapted for fixing on a side body of said treated patient to retain said side body thereof at a fixation position and for providing a retraction force against said side body of said treated patient; and
a curvature adjusting device provided on said supporting frame to adjustably retain a distance between said first and second end portions of said guiding frame so as to selectively adjust a curvature of said guiding surface with respect to said supporting frame for fitting on said side body of said treated patient, wherein said curvature adjusting device contains a plurality of engaging slots spacedly provided on said body supporting member, wherein said first end portion of said guiding frame is securely affixed to said body supporting member and said second end portion of said guiding frame is selectively engaged with one of said engaging slots so as to adjust said distance between said first and second end portions of said guiding frame and said curvature of said guiding surface thereof.

4. An ambulatory hip fixation-traction splint set, comprising:
a supporting frame comprising a body supporting member having an upper end arranged for positioning below an armpit of a treated patient and a lower end extending to position below a hip portion of said treated patient, wherein said supporting frame further comprises a ground supporting member comprising a ground stand downwardly extended from said body supporting member for distributing a weight of said treated patient through said ground stand; wherein said ground stand is slidably extended from said body supporting member, wherein said supporting frame further comprises a locking member provided at said body supporting member to lock up said body supporting member with said ground stand so as to selectively adjust a supportive portion of said ground stand from said body supporting member with respect to a height of said treated patient, wherein said supporting frame further comprises an armpit resting support mounted at said upper end of said body supporting frame for supporting said armpit of said treated patient, and a supporting footstep transversely extended from said ground stand above a ground end thereof for substantially supporting said treated patient's foot; and
a side splint assembly, which comprises:
a flexible guiding frame having first and second end portions mounted to said upper and lower ends of said body supporting member respectively wherein said guiding frame has a curved guiding surface adapted for fixing on a side body of said treated patient to retain said side body thereof at a fixation position and for providing a retraction force against said side body of said treated patient; and
a curvature adjusting device provided on said supporting frame to adjustably retain a distance between said first and second end portions of said guiding frame so as to selectively adjust a curvature of said guiding surface with respect to said supporting frame for fitting on said side body of said treated patient, wherein said curvature adjusting device contains a plurality of engaging slots spacedly provided on said body supporting member, wherein said first end portion of said guiding frame is securely affixed to said body supporting member and said second end portion of said guiding frame is selectively engaged with one of said engaging slots so as to adjust said distance between said first and second end portions of said guiding frame and said curvature of said guiding surface thereof.

5. The ambulatory hip fixation-traction splint set, as recited in claim 4, further comprising a front splint assembly comprising a side supporting member, a side extension frame transversely extended from said body supporting member to securely connect to said side supporting member, and a flexible front guiding frame having first and second end portions spacedly mounted to said side supporting member and a curved front guiding surface adapted for fixing on a front body of said treated patient to retain said front body thereof at a fixation position.

6. An ambulatory hip fixation-traction splint set, comprising:
a supporting frame comprising a body supporting member having an upper end arranged for positioning below an armpit of a treated patient and a lower end extending to position below a hip portion of said treated patient;
a side splint assembly comprising a flexible guiding frame having first and second end portions mounted to said upper and lower ends of said body supporting member respectively wherein said guiding frame has a curved guiding surface adapted for fixing on a side body of said treated patient to retain said side body thereof at a fixation position and for providing a retraction force against said side body of said treated patient; and
a front splint assembly comprising a side supporting member, a side extension frame transversely extended from said body supporting member to securely connect to said side supporting member, and a flexible front guiding frame having first and second end portions spacedly mounted to said side supporting member and a curved front guiding surface adapted for fixing on a front body of said treated patient to retain said front body thereof at a fixation position.

7. An ambulatory hip fixation-traction splint set, comprising:

a supporting frame comprising a body supporting member having an upper end arranged for positioning below an armpit of a treated patient and a lower end extending to position below a hip portion of said treated patient;

a side splint assembly comprising a flexible guiding frame having first and second end portions mounted to said upper and lower ends of said body supporting member respectively wherein said guiding frame has a curved guiding surface adapted for fixing on a side body of said treated patient to retain said side body thereof at a fixation position and for providing a retraction force against said side body of said treated patient, wherein said side splint assembly further comprises a curvature adjusting device provided on said supporting frame to adjustably retain a distance between said first and second end portions of said guiding frame so as to selectively adjust a curvature of said guiding surface with respect to said supporting frame for fitting on said side body of said treated patient; and a front splint assembly comprising a side supporting member, a side extension frame transversely extended from said body supporting member to securely connect to said side supporting member, and a flexible front guiding frame having first and second end portions spacedly mounted to said side supporting member and a curved front guiding surface adapted for fixing on a front body of said treated patient to retain said front body thereof at a fixation position.

8. An ambulatory hip fixation-traction splint set, comprising:

a supporting frame comprising a body supporting member having an upper end arranged for positioning below an armpit of a treated patient and a lower end extending to position below a hip portion of said treated patient, wherein said body supporting member comprises an upper tubular body and a lower tubular body slidably and coaxially mounted to said upper tubular body so as to adjust said distance between said first and second end portions of said guiding frame, wherein said curvature adjusting device comprises a frame locker mounted on said body supporting member to lock up said upper tubular body with said lower tubular body so as to securely retain said distance between first and second end portions of said guiding frame and selectively adjust said curvature of said guiding surface thereof, wherein said supporting frame further comprises a ground supporting member comprising a ground stand downwardly extended from said body supporting member for distributing a weight of said treated patient through said ground stand, wherein said ground stand is slidably extended from said body supporting member, wherein said supporting frame further comprises a locking member provided at said body supporting member to lock up said body supporting member with said ground stand so as to selectively adjust a supportive portion of said ground stand from said body supporting member with respect to a height of said treated patient, wherein said supporting frame further comprises an armpit resting support mounted at said upper end of said body supporting frame for supporting said armpit of said treated patient, and a supporting footstep transversely extended from said ground stand above a ground end thereof for substantially supporting said treated patient's foot;

a side splint assembly comprising a flexible guiding frame having first and second end portions mounted to said upper and lower ends of said body supporting member respectively wherein said guiding frame has a curved guiding surface adapted for fixing on a side body of said treated patient to retain said side body thereof at a fixation position and for providing a retraction force against said side body of said treated patient; wherein said side splint assembly further comprises a curvature adjusting device provided on said supporting frame to adjustably retain a distance between said first and second end portions of said guiding frame so as to selectively adjust a curvature of said guiding surface with respect to said supporting frame for fitting on said side body of said treated patient; and a front splint assembly comprising a side supporting member, a side extension frame transversely extended from said body supporting member to securely connect to said side supporting member, and a flexible front guiding frame having first and second end portions spacedly mounted to said side supporting member and a curved front guiding surface adapted for fixing on a front body of said treated patient to retain said front body thereof at a fixation position.

* * * * *